United States Patent [19]

Lezdey et al.

[11] Patent Number: 5,166,134

[45] Date of Patent: * Nov. 24, 1992

[54] TREATMENT OF ALLERGIC RHINITIS

[76] Inventors: John Lezdey, 976 Kingston Dr., Cherry Hill, N.J. 08034; Allan J. Wachter, 9822 S. Grandview, Tempe, Ariz. 85284

[*] Notice: The portion of the term of this patent subsequent to Apr. 16, 2008 has been disclaimed.

[21] Appl. No.: 710,055

[22] Filed: Jun. 4, 1991

Related U.S. Application Data

[63] Continuation-in-part of Ser. No. 598,241, Oct. 16, 1990, and a continuation-in-part of Ser. No. 591,630, Oct. 2, 1990, which is a continuation-in-part of Ser. No. 445,005, Dec. 4, 1989, Pat. No. 5,008,242, and a continuation-in-part of Ser. No. 181,707, Sep. 8, 1988, abandoned, which is a continuation-in-part of Ser. No. 946,445, Dec. 24, 1986, abandoned.

[51] Int. Cl.$^5$ .............................................. A61K 37/64
[52] U.S. Cl. ........................................ 514/8; 514/2; 514/12; 514/21
[58] Field of Search ........................... 514/218, 12, 21

[56] References Cited

U.S. PATENT DOCUMENTS

| | | | |
|---|---|---|---|
| 4,636,489 | 1/1987 | Seemuller et al. | 514/12 |
| 4,732,973 | 3/1988 | Barr et al. | 530/350 |
| 4,857,314 | 8/1989 | O'Connor et al. | 514/2 X |
| 4,916,117 | 4/1990 | Lezdey et al. | 514/8 |
| 5,008,242 | 4/1991 | Lezdey et al. | 514/8 |

OTHER PUBLICATIONS

Hubbard et al, Biochemical Efficacy and Safety of Monthly Augmentation Therapy for Alpha 1-Antitrypsin Deficiency–Sep. 2, 1988–vol. 260, No. 9.

*Primary Examiner*—Howard E. Schain
*Attorney, Agent, or Firm*—John Lezdey

[57] ABSTRACT

A method for the prophylaxis or direct treatment of allergic rhinitis which comprises nasally administering to a patient an effective amount of a serine protease inhibitor which inhibits mast cells, neutrophiles or T-cells or binds with their mediators.

5 Claims, No Drawings

TREATMENT OF ALLERGIC RHINITIS

RELATED APPLICATION

This application is a continuation-in-part of application Ser. No. 598,241 filed Oct. 16, 1990, of Lezdey et al and application Ser. No. 591,630 filed Oct. 2, 1990, which is a continuation-in-part of application Ser. No. 445,005 filed Dec. 4, 1989 (now U.S. Pat. No. 5,008,242) which is a continuation-in-part of application Ser. No. 242,735 filed Sep. 9, 1988, now abandoned, and application Ser. No. 181,707 filed Sep. 8, 1988, now abandoned, which are continuations-in-part of application Ser. No. 946,445 filed Dec. 24, 1986, now abandoned.

FIELD OF THE INVENTION

The present invention relates to the treatment of allergic rhinitis utilizing serine protease inhibitors. More particularly, there is provided a means for treating allergic rhinitis and for inactivating at the site of administration the proteases which stimulate histamine release and result in nasal discomforture.

BACKGROUND OF THE INVENTION

Pollen has long been recognized as a cause of allergic rhinitis commonly called "hay fever". Pollen contains proteases which induce the release of mediators from mast cells stimulates IgE brosynthesis. The degranulation of mast cells by IgE results in the release of histamines which leads to an inflammatory response which causes congestion, itching swelling of sinuses. Many eosinophils are present in allergic patients with nasal mucus and neutrophils are present in patients with infected muscus.

Antihistamines are drugs commonly utilized which are taken orally that have a sedative effect. Alternatively, nasal sprays of the antihistamines can be utilized. However, such sprays have not been found to be long lasting and effective during the pollen season. Nasal sprays containing cromolyn sodium have been effective since cromolyn acts by blocking the reaction of allergen with tissue mast cells. However, cromolyn is not entirely effective since it apparently does not bind with some of the mediators of inflammation or the activators of IgE biosynthesis that stimulate the degranulation of mast cells and the production of histamines from the mast cells.

Inflammation is a non-specific response of tissues to diverse stimuli or insults and results in release of a variety of materials at the site of inflammation that induce pain. It is now recognized that mast cells, neutrophils and T-cells are implicated in the pathophysiology of inflammatory skin conditions as well as in other physiological disorders. Mast cells provide the greatest source of histamines in acute inflammation, as well as chymases, after degranulation by IgE. Serine protease inhibitors such as $\alpha_1$-antitrypsin and $\alpha_1$-antichymotrypsin have been found to be useful in the treatment of dermatitis by inhibiting and/or binding with elastase, cathepsin G and human mast cell chymase.

Alpha 1-antichymotrypsin is a plasma protease inhibitor synthesized in the liver. It is a single glycopeptide chain of approximately 68,000 daltons and belongs to a class of serine protease inhibitors with an apparent affinity toward chymotrypsin-like enzymes. Alpha 1-antichymotrypsin is structurally related to alpha 1-antitrypsin.

Alpha 2-macroglobulin is a glycoprotein containing 8–11% carbohydrate which can be isolated from plasma by gel filtration chromatography.

Alpha 1-proteinase inhibitor (alpha 1-antitrypsin) is a glycoprotein having a molecular weight of 53,000 determined by sedimentation equilibrium centrifugation. The glycoprotein consists of a single polypeptide chain to which several oligosaccharide units are covalently bonded. Human alpha 1-proteinase inhibitor has a role in controlling tissue destruction by endogenous serine proteinases. A genetic deficiency of alpha-1-proteinase inhibitor, which accounts for 90% of the trypsin inhibitory capacity in blood plasma, has been shown to be associated with the development of asthma and pulmonary emphysema. The degradation of elastin associated with certain inflammatory diseases probably results from a local imbalance of elastolytic enzymes and the naturally occurring tissue and plasma proteinase inhibitors. Alpha-1-proteinase inhibitor inhibits human pancreatic and leukocyte elastases. See Pannell et al, Biochemistry. 13, 5339 (1974); Johnson et al, Biochem. Biophys. Res. Commun., 72 33 (1976); Del Mar et al, Biochem. Biophys. Res. Commun., 88, 346 (1979); and Heimburger et al, Proc. Int. Res. Conf. Proteinase Inhibitors. 1st, 1–21 (1970).

The article of Groutas entitled "Inhibitors of Leukocyte Elastase and Leukocyte Cathepsin G Agents for the Treatment of Emphysema and Related Ailments" Medical Research Reviews, Vol. 7, No. 7, 227–241 (1987), discloses the role of eglin, elastinal 1 and elastin in emphysema.

U.S. Pat. No. 4,916,117 to Lezdey et al discloses the treatment of pulmonary inflammation where mast cells are involved with microcrystalline alpha-1-antichymotrypsin alone or with other serine protease inhibitors.

U.S. Pat. No. 4,732,973 to Barr et al, herein incorporated by reference which discloses active site modified protease $\alpha$-1-antitrypsin inhibitors which can be used in the present invention.

It is understood that the term "serine protease inhibitors" as used herein is meant to include the analogs, derivatives or salts, which are derived naturally or by recombinant technology.

SUMMARY OF THE INVENTION

The present invention provides a method for the prophylactic and direct treatment of patients suffering from allergic rhinitis and the symptoms thereof. In accordance with the invention, there is nasally administered to the patient an effective amount of a serine protease inhibitor or acute phase reactant, its analog, derivative or salt in a suitable pharmaceutically acceptable carrier. The serine protease inhibitors, analog, derivative or salt is one which is capable of binding with a protease in pollen, a protease derived from mast cells, neutrophils or T-cells or decreasing the degranulation of mast cells.

Preferably, the serine protease inhibitor is administered in an aqueous solution comprising 0.1 to 4.5% by weight of the inhibitor. A greater amount can be used but is generally not required.

Advantageously, the serine protease inhibitor binds with a stimulator of IgE synthesis and inhibits mast cell degranulation. These inhibitors further prevent protease from activating complement and kinins which cause the discomfiture associated with the disease.

The term "allergic rhinitis" is understood to include rhinitis medicamentosa, rhinitis sicca and atrophic rhinitis. Preferable are the serine protease inhibitors which have a specific inhibiting activity of mast cell proliferation or degranulation and are binding with the proteases derived therefrom such as cathepsin-G, elastase, human mast cell chymase, kinins, and the like. The inhibiting activity may be direct or indirect. It has now been found that controlling the amount of mast cells and their mediators inherently controls the amount of the enzymes at the site of inflammation and prevents proliferation of the condition. Serine protease inhibitors or acute phase reactants, for example, alpha-1-antitrypsin alpha 2-macroglobulin, alpha 1-antichymotrypsin or C-reactive protein (CRP), when administered to the site of inflammation provides a reduction in swelling of the sinuses.

The serine protease inhibitors which are contemplated in the present invention are any of the inhibitors, their analogs, derivatives or salts and glycosylated or nonglycosylated recombinant compounds which can inhibit mast cells or bind with any one or more of the protease derived from eosinophils, basophils and/or neutrophils such as elastase, cathepsin-G, tryptase, chymase, kinin, kallikrein, chymotrypsin, collagenase, and the like.

The serine protease inhibitors and/or acute phase reactants included in the present invention are alpha 1-antichymotrypsin, alpha 1-antitrypsin, alpha 2-macroglobulin, eglin, elastinal 1, elasnin 3, C-reactive protein, beta 1-antigellagenase, serine amyloid A protein, alpha cysteine protease inhibitors, inter-alphatrypsin inhibitor, secretory leucocyte protease inhibitor, bronchial mucous inhibitor, and C-1-inhibitor. The inhibitors of the invention may be natural or prepared by recombinant means.

Eglin is particularly effective in binding with tryptase.

Alpha 1-antitrypsin has also been found especially useful because of its association with elastase and kinins. However, it is preferably used in combination with alpha 1-antichymotrypsin if the patient smokes.

The serine protease inhibitors of the invention may be prepared by cloning, by conventional techniques utilizing an oligonucleotide probe or antibody probe, and the like. Analogs may be prepared using site specific mutagenesis using conventional processes. The recombinant gene product of the invention is especially useful since it is free of contaminating viruses when produced.

The analogs, salts and derivatives may be formed utilizing conventional techniques associated with other proteins without effecting the utility of the compound. There may be prepared the alkali metal salts, acid-addition salts, and esters similar to other proteins or peptides.

It is desirable to administer in some case a combination or cocktail of the serine protease inhibitors to provide a broad spectrum of drugs which can provide rapid relief of the different symptoms and because of the different proteases found in pollen. The most effective combination is alpha 1-antichymotrypsin and alpha 1-antitrypsin and/or alpha 2-macroglobulin. Preferably, the combination is administered in a ratio of 1:1:1: to 3:2:1: either in a single unit or in separate dosage form.

It is therefore an object of the invention to provide a composition which can relieve the symptoms of allergy associated with allergic rhinitis.

It is a yet still further object of the invention to provide a method and a composition for treating allergic rhinitis and as a prophylaxis.

DETAILED DESCRIPTION OF THE PRESENT INVENTION

The objects of the present invention can be achieved by the nasal administration of an affective amount of a serine protease inhibitor or acute phase reactant in a suitable pharmaceutical form to patients suffering from allergic rhinitis or subjected to pollen causing the condition. In accordance with one method of treatment, 0.1% to 2.5% by weight of a solution such as a serine protease inhibitor, particularly $\alpha$ 1-antitrypsin, alone or in combination with other serine protease inhibitors such as $\alpha_1$-antichymotrypsin, in a sterile water or saline solution, may be used by the patient as a nose drop or nasal spray.

The pharmaceutical compositions may be prepared for nasal administration according to standard formulating procedures. The serine protease inhibitor can be dissolved in purified water or a saline solution.

It is preferred to include a preservative, for example, Thimerosal or benzalkonium chloride and an antioxidant, for example, vitamin E. Other filler materials which can be included and are commonly found in nasal compositions include sodium carbonate solution, sorbitol solution, polyethylene glycol and the like.

The compositions are generally administered every four to eight hours and/or as conditions of the patient and atmosphere require.

The following examples further illustrate the practice of this invention, but are not intended to be limiting thereof. It will be appreciated that the selection of actual amounts of mast cell inhibitors to be administered to any individual patient will fall within the discretion of the attending physician and will be prescribed in a manner commensurate with the appropriate dosages will depend on the stage of the disease and like factors uniquely within the purview of the attending physician.

EXAMPLE 1

A composition which is effective for use as a nasal spray or nose drops was prepared as with the following ingredients:

| Ingredient | % wt |
|---|---|
| $\alpha_1$-antitrypsin | 0.1 |
| 10% saline solution | 99.8 |
| antioxidant | 0.1 |

In lieu of $\alpha_1$-antitrypsin, valine analog of $\alpha_1$-antitrypsin may be utilized or $\alpha_1$-antichymotrypsin.

EXAMPLE 2

A 10 ml solution which is effective for use as a nasal spray or nose drops was prepared with the following ingredient:

| Ingredient | Wt |
|---|---|
| $\alpha_1$-antitrypsin | 2.5 mg |
| $\alpha_1$-antichymotrypsin | 2.5 mg |
| sorbitol solution | 571.0 mg |
| vitamin E | 2.0 mg |
| purified water | q.s. |

EXAMPLE 3

A 0.15% by weight solution of PROLASTIN, a composition sold by Cutter Biological, Miles Inc., comprising about 70% $\alpha_1$-antitrypsin and about 10-18% $\alpha_1$-antichymotrypsin with a 10% saline solution. The solution prepared could be packaged for use as a nasal spray or as nose drops.

EXAMPLE 4

Three (3) patients suffering from allergic rhinitis and all have the symptoms of congestion, runny nose and nasal irritation were each treated by spraying into each nasal passage the composition of Example 3.

After twenty (20) minutes each of the patients showed signs of free breathing and no longer having a runny nose. The patients after four hours and without any further administration did not suffer any relapse even when expose to a pollen laden atmosphere.

What is claimed is:

1. A method for the treatment of a patient suffering from allergic rhinitis which comprises nasally administering an effective amount of at least one serine protease inhibitor or acute phase reactant, its salts, derivatives or analogs selected from the group consisting of $\alpha_1$-antitrypsin and $\alpha_1$-antichymotrypsin in a suitable pharmaceutically acceptable carrier.

2. The method of claim 1 wherein said serine protease inhibitor binds with a stimulator of IgE synthesis.

3. The method of claim 1 wherein said serine protease inhibitor is a combination of $\alpha_1$-antitrypsin and $\alpha_1$-antichymotrypsin.

4. The method of claim 1 which comprises administering an aqueous solution of about 0.1 to 2.5% by weight of said serine protease inhibitor.

5. The method of claim 1 wherein said serine protease inhibitor is recombinant.

* * * * *